United States Patent [19]

Imahori et al.

[11] Patent Number: 4,882,276

[45] Date of Patent: Nov. 21, 1989

[54] PROCESS FOR PRODUCING PHYSIOLOGICALLY ACTIVE SUBSTANCE BY MULTIENZYME PROCESS

[75] Inventors: Kazutomo Imahori, Tokyo; Hitoshi Kondo, Kyoto; Hiroshi Nakajima, Kyoto; Tatsuo Iwasaki, Kyoto, all of Japan

[73] Assignees: Kazutomo Imahori; Rikagaku Kenkyusho; Unitika Ltd., all of Japan

[21] Appl. No.: 461,308

[22] Filed: Jan. 26, 1983

[30] Foreign Application Priority Data

May 27, 1982 [JP] Japan ................................ 57-90424

[51] Int. Cl.[4] ...................... C12P 19/30; C12P 19/40; C12Q 3/00
[52] U.S. Cl. ........................................ 435/89; 435/88; 435/92; 435/3; 435/813
[58] Field of Search ...................... 435/88, 89, 92, 813, 435/3, 824, 842, 886, 887, 906, 832, 833

[56] References Cited

U.S. PATENT DOCUMENTS

| 3,846,239 | 7/1972 | Detente .................. 195/66 |
| 3,979,261 | 9/1976 | Outtrup .................. 195/65 |
| 4,011,139 | 3/1977 | Horwarth et al. .................. 195/65 |
| 4,164,444 | 1/1977 | Whiteside et al. .................. 435/92 |
| 4,220,722 | 9/1980 | Rowley et al. .................. 435/188 |
| 4,313,938 | 2/1982 | Arimura et al. .................. 424/180 |
| 4,342,827 | 8/1982 | Atkinson .................. 435/26 |
| 4,424,278 | 1/1984 | Bucovaz et al. .................. 436/501 |

OTHER PUBLICATIONS

Langer et al AIChE Journal v. 23, No. 1, pp. 1–9, Jan. 1977, "Enzymatic Regeneration of ATP".
Unitika Ltd Chem. Abstr v. 94, No. 119487v 1981 p. 533 "Microbial cells containing high level of acetate kinase".
Nakajima et al Chem Abstr v. 89, No. 10257s 1978 pp. 331–332 "Purification and properties of acetate kinase from Bacillus stearothermophilus".
Dixon Malcolm Enzymes Academic Press NY 1964 pp. 146–147.

Primary Examiner—Thomas G. Wiseman
Assistant Examiner—Robin Lyn Teskin
Attorney, Agent, or Firm—Sughrue, Mion, Zinn, Macpeak, and Seas

[57] ABSTRACT

A process for converting AMP into ATP which comprises (a) using an enzyme which converts AMP into ADP and has been produced from microorganisms having an optimum growth temperature of 50° C. to 85° C. and an enzyme which converts ADP into ATP and has been produced from microorganisms having an optimum growth temperature of 50° to 85° C. is disclosed. In addition, there is disclosed a process for producing a physiologically active substance by a multienzyme process which comprises forming ATP from AMP by the step (a), (b) synthesizing a physiologically active substance with the resulting ATP, coverting AMP resulting from the reaction in step (b) into ATP by the reaction in step (a), and repeatedly utilizing the converted ATP for synthesis of the physiologically active substance in step (b). By using the process it is possible to stably and efficiently carry out conversion of AMP into ATP over a long period of time. Further, it is possible to carry out continuously and economically an enzymic reaction using ATP as an auxiliary factor with very good efficiency. Whereby it has become possible to practically operate the so-called bioreactor wherein synthetic reactions in the living body are carried out as industrial chemical reactions outside the living body.

2 Claims, No Drawings

PROCESS FOR PRODUCING PHYSIOLOGICALLY ACTIVE SUBSTANCE BY MULTIENZYME PROCESS

FIELD OF THE INVENTION

The present invention relates to a process for converting adenosine-5'-monophosphate (hereinafter referred to as AMP) into adenosine-5'-triphosphate (hereinafter referred to as ATP) and a process for producing a physiologically active substance by an enzymic reaction using ATP as an auxiliary factor.

BACKGROUND OF THE INVENTION

In recent years, chemical reactions of living bodies have been closely examined in order to attempt to reproduce the chemical reactions of living bodies in a reactor. In living bodies, many biosynthetic reactions are naturally performed in the presence of enzymes as a catalyst in order to support life. Accordingly, living bodies easily produce compounds which are difficult to synthesize by chemical reactions. Knowledge of such reaction is becoming important for satisfying social requirements such as conserving energy and eliminating public nuisances. Reproducing such reactions will likely become an essential technique in chemical industries. The practical use of such reactions has already been found useful in the technical fields of hydrolysis and isomerization.

When carrying out a synthetic reaction (which is a particularly important reaction in biosynthetic reactions), ATP is required as an energy source or an auxiliary factor. In such reactions, ATP is consumed by decompressing into adenosine-5'-diphosphate (hereinafter referred to as ADP) or adenosine-5'-monophosphate after it serves as an energy source or an auxiliary factor. Accordingly, in order to industrially reproduce the synthetic reaction, it is necessary to supply ATP at a moderate price. However, ATP is a very expensive substance. Accordingly, it is important to convert ADP and AMP which are in a state after consumption and, particularly, AMP which is in a consumed state of the lowest energy level, into ATP.

Many studies concerning reproduction and conversion into ATP have been done. For example, since production of ATP is carried out by a glycolysis reaction in the living bodies, an attempt utilizing such a reaction is known in T. Tochikura, M. Kuwahara, S. Yagi, H. Okamoto, Y. Tominaga, T. Kano and K. Ogata, *J. Ferment. Tech.*, 45, 511 (1967); H. Samejima, K. Kimura, Y. Ado, Y. Suzuki and T. Tadokoro, *Enzyme Eng.*, 4, 237 (1978) and M. Asada, K. Yanamoto, K. Nakanishi, R. Matsuno and T. Kamikubo, *Eur. J. Appl. Microbial. Biotechnol.*, 12, 198 (1981). The concept of the reaction is that reproduction and supply of consumed ATP are carried out using microorganisms, wherein AMP or adenosine is used as a raw material for ATP. However, since the AMP or adenosine is not a product after consumption of ATP, it is additionally added as an ATP source. As a result of this attempt, the conversion efficiency of AMP or adenosine into ATP is very inferior and side reactions are caused. Specifically, when utilizing glycolysis of microorganisms, negative result is only obtained concerning effective reproduction of ATP from AMP which is a product after consumption of ATP.

The use of an ATP conversion enzyme which is not a heat-resisting enzyme has been attempted. Langer et al. have reported process in converting AMP into ATP by means of adenylate kinase in rabbit muscles and acetate kinase in Escherichia coli in R. S. Langer, B. K. Hamilton, C. R. Colton, *AlchE J.*, 23, 1 (1977); and U.S. Pat. No. 4,164,444. Further, reports have been made with respect to converting adenosine into ATP using adenosine kinase in addition to the above described two kinds of conversion enzyme in R. L. Baughn, O. Adalsteinsson and G. M. Whitesides, *J. Am. Chem. Soc.*, 100, 304 (1978). Furthermore, Whitesides et al. have reported that, when the above-described adenylate kinase and acetate kinase are immobilized to Sepharose with cyanogen bromide to continuously convert AMP into ATP, the residual activity is only several percentages or less in the absence of a stabilizer and stability with the passage of time is remarkably inferior as described in G. m. Whitesides, A. Chmurny, P. Garrett and C. K. Colton, *Enzyme Eng.*, 2, 217 (1974). Moreover, even if an immobilized enzyme is used and a stabilizer is added, the reaction requires a long period of time and conversion efficiency is not so high, and it cannot be utilized for operating under a level of chemical industry for a long period of time.

However, little is known with respect to the production of useful substances by the above-described synthetic reaction with reproducing ATP. There is a process which comprises reproducing ATP which was consumed when synthesizing glutathione by reacting glutamic acid, cystein and glycine with γ-glutamyl cystein synthesis enzyme and glutathione synthesis enzyme, from ADP which is a product after consumption by a function of acetate kinase originated from Escherichia coli and using it again (as described in K. Murata, K. Tani, J. Kato and I. Chibata, *Eur. J. Microbial Biotechnol.*, 10, 11 (1980)). However, this process does not provide any information with respect to converting the above-described AMP consumed to the lowest energy level into ATP, because it is only a process for reproducing ATP from /ADP.

A bioreactor for synthesizing a useful substance by continuously consuming ATP into AMP has been considered, and it has been highly desired to complete such a system as described in G. M. Whitesides, A. Chmurny, P. Garrett, L. Lamotte and C. K. Colton, *Enzyme Eng.*, 2, 217 (1974).

SUMMARY OF THE INVENTION

An object of the present invention is to provide a process for converting AMP (which is a product obtained by decomposing ATP to the lowest energy level) into ATP in a high yield. Another object of the present invention is to provide a process for producing a physiologically active substance by a multienzyme process which comprises using AMP which is a product obtained by decomposing to the lowest energy level as a raw material.

As a result of earnest studies so as to attain the above-described objects, the present inventors have found that AMP can be converted into ATP in a high yield in a short period of time, when conversion enzymes produced from microorganisms having an optimum growth temperature of 50° C. to 85° C. are used. As a result of subsequent studies, we have found, on the basis of the above-described knowledge, that a physiologically active substance can be synthesized from AMP which is a product obtained by decomposing to the lowest energy level as a raw material, by combining (a)

a reaction system of converting AMP into ATP with (b) a reaction system of synthesizing a physiologically active substance from ATP.

The present invention relates to a process for converting AMP into ATP which comprises using, as conversion enzymes, an enzyme which converts AMP into ADP, the enzyme having been produced from microorganisms having an optimum growth temperature of 50° C. to 85° C., and an enzyme which converts ADP into ATP, the enzyme having been produced from microorganisms having an optimum growth temperature of 50° C. to 85° C. In addition, the invention relates to a process for producing a physiologically active substance by a multienzyme process which comprises (a) forming ATP from AMP using a combination of an enzyme which converts AMP into ADP and has been produced from microorganisms having an optimum growth temperature of 50° C. to 85° C. and an enzyme which converts ADP into ATP and has been produced from microorganisms having an optimum growth temperature of 50° C. to 85° C., (b) synthesizing a physiologically active substance with the resulting ATP, converting AMP resulting from the reaction in the step (b) into ATP by the reaction in the step (a), and repeatedly utilizing the converted ATP for synthesis of the physiologically active substance in step (b).

According to the present invention, it becomes possible to stably carry out conversion of AMP into ATP efficiently over a long period of time. Further, it is possible to continuously and economically carry out an enzymic reaction using ATP as an auxiliary factor with very good efficiency, whereby it becomes possible to realize operation of the so-called bioreactor wherein synthetic reactions in the living body are carried out as industrial chemical reactions outside the living body.

DETAILED DESCRIPTION OF THE INVENTION

The present invention comprises conversion of AMP into ADP and conversion of the resulting ADP into ATP. For example, adenylate kinase is used as an enzyme for converting AMP into ADP, and ATP is used as a phosphoric acid donator in this case. Examples of enzymes for converting ADP into ATP include acetate kinase, carbamate kinase, creatine kinase, 3-phosphoglycerate kinase, pyruvate kinase and polyphosphate kinase. Acetate kinase is preferably used considering the price of phosphoric acid donator, activity for converting into ATP and availability of enzymes, etc. In this case, acetylphosphate is used as a phosphoric acid donator. As described above, though ATP and acetyl phosphate are used as phosphoric acid donators when using adenylate kinase and acetate kinase, it is sufficient to supply only acetyl phosphate as the phosphoric acid donator, because ATP as the final conversion product can be used as the phosphoric acid donator. From the application of the above-described advantages which are obtained when using the acetate kinase alone and when using the combination of acetate kinase and adenylate kinase, it becomes possible to plan the system in which the ATP is effectively reproduced from the AMP.

As described above, it becomes possible to convert AMP into ATP using two kinds of conversion enzymes. However, these enzymes are those produced from microorganisms having an optimum growth temperature of 50° C. to 85° C. Examples of such microorganisms include microorganisms of the genus Bacillus, such as *Bacillus stearothermophillus, Bacillus brevis, Bacillus coagulans, Bacillus thermoproteolyticus* or *Bacillus acidocaldarius*, etc., microorganisms of the genus Clostridium, microorganisms of the genus Thermoactinomyces, microorganisms of the genus Achromobacter, microorganisms of the genus Streptomyces, microorganisms of the genus Micropolyspora, microorganisms of the genus Thermus such as *Thermus aquaticus, Thermus thermophilus* or *Thermus flavus*, etc., microorganisms of the genus Thermomicrobium, etc. Further, there are microorganisms growing at a normal temperature into which genes of the above-described microorganisms are introduced. Among these microorganisms, *Bacillus stearothermophilus* is particularly suitable for producing both enzymes of adenylate kinase and acetate kinase. Both enzymes obtained from this microorganism can be easily purified and have a high specific activity. In the present invention, it is preferred to use the above-described enzymes in an immobilized state. For this purpose, the enzymes are bonded to, included in or absorbed in suitable carriers. Examples of such carriers include polysaccharide derivatives such as cellulose, dextran or agarose, etc., vinyl polymer derivatives such as polystyrene, ethylene-maleic acid copolymer or cross-linked polyacrylamide, etc., polyaminoacids and polyamide derivatives such as L-alanine-L-glutamic acid copolymer or polyaspartic acid, etc., and inorganic derivatives such as glass, alumina or hydoxyapatite, etc., preferably polysaccharide derivatives, inorganic derivatives such as glass and vinyl polymer derivatives such as polystyrene, which are used by packing a reactor such as a column therewith. The preferred amount of the above carriers used per the enzyme is 1 μg/enzyme unit to 100 g/enzyme unit (indicated by enzyme activity unit), more preferably 10 μg/enzyme unit to 10 g/enzyme unit.

In order to convert AMP into ATP according to the present invention, it is preferred to carry out conversion of AMP→ADP→ATP in a packed bed reactor by feeding 0.1 μM to 4M, preferably 1 μM to 2M and, more preferably 10 μM to 500 mM of AMP, 0.1 μM to 500 mM, preferably 1 μM to 400 mM and, more preferably 10 ∞M to 300 mM of acetyl phosphate, and ATP to an end of the reactor. In this case, it is particularly preferred to use ATP in an amount satisfying the formula (a).

$$0.15 \times \frac{5 + r^2}{r^2} \times AMP \geqq ATP \geqq 0.04 \times \frac{5 + r^2}{r^2} \times AMP \quad (a)$$

(wherein AMP represents the concentration of AMP (mM), ATP represents the concentration of ATP (mM), and r represents a ratio of immobilized enzyme activity of the enzyme which converts ADP into ATP to immobilized enzyme activity of the enzyme which converts AMP into ADP, which is a positive integer of 1 or more). The reacting solution eluted from the reactor in this case can be analyzed by a suitable analyzing system to determine concentrations of AMP, ADP and ATP and a conversion to ATP. In this case, the flow rate varies according to the size of the reactor. For example, a suitable flow rate can be selected from the linear velocity range of $1 \times 10^{-4}$ cm/hr to $1 \times 10^6$ m/hr. When using the 5 liters reactors having inside diameter of 10 cm and length of 63.5 cm, it is preferred to select a suitable flow rate from the linear velocity range of $6 \times 10^{-2}$ cm/hr to $1 \times 10^5$ cm/hr. The apparatus for supplying AMP, ATP and acetyl phosphate to the reactor are not particularly restricted, if they are capable of varying the amount of sending flow by external control signals. For example, metering pumps driven by a pulse motor can be used (referred to as variable fluid sending apparatus, hereinafter). Further, flow rates and concentrations of solutions of each substrate can be varied by providing automatic controlling valves between vessels containing the solutions of each substrate and variable fluid sending apparatus, and controlling opening and closing of the automatic controlling valves by external signals. The automatic controlling valves may be electromagnetic valves. Further, the reactor may be used, of course, at an ambient temperature. However, it is preferable to add a means for maintaining any given temperature. The analyzing system for analyzing the reacting solution from the reactor is not particularly restricted, if AMP, ADP and ATP are detected. An example of a preferred system is a high performance liquid chromatographic apparatus.

In the present invention, in order to carry out industrially, stably and economically substantial 100% conversion of AMP into ATP over a long period of time, it is preferred to control the concentration of ATP so as to satisfy the formula (a), and it is particularly preferred to control the concentration of ATP so as to be $$0.08 \times \frac{5 \pm r^2}{r^2} \times$$

AMP or less in addition to the formula (a). In order to satisfy the formula (a), the following method can be used. Namely, control may be carried out by a method which comprises previously feeding the formula (a) and data necessary for operation to an arithmetical control unit, carrying out operation of conversion of AMP into ATP from the above-described formula and data and analyzed data from the analyzing system, and sending signals from the arithmetical control unit to at least one of the above-described variable fluid sending apparatus and the automatic controlling valve to vary the flow rate or the concentration so as to satisfy the formula (a). In this case, data necessary for carrying out operation means the concentrations of the AMP and ATP a raw materials and the ratio of the immobilized enzyme activity of the enzyme for converting ADP into ATP to the immobilized enzyme activity of the enzyme for converting AMP into ADP, and analyzed data means the concentrations of AMP, ADP and ATP in the reacting solution from the reactor. Further, the arithmetical control unit refers to an apparatus having an arithmetical function and a function of sending control signals to an external apparatus. For example, a microcomputer can be used. Further, the immobilized enzyme activity means activity of the immobilized enzyme. For example, in case of adenylate kinase, activity in the direction of AMP+ATP→2.ADP is shown. With respect to acetate kinase, activity in the direction of ADP+acetyl phosphate→ATP+acetic acid is shown. In order to measure the activity, a desired amount of the immobilized enzyme, for example, 5 to 10 μl according to degree of activity, is added to a solution for measuring activity, and activity is measured by pursuing it as a change in absorbance by means of a spectrophotometer by the same manner as in case of free enzyme. 1 unit of enzyme activity means the amount of producing 1 micromole of ADP per minute at 30° C. in case of adenylate kinase and the amount of producing 1 micromole of ATP per minute in case of acetate kinase.

The ATP used in the present invention may be the ATP which is the final conversion product of the above-described reaction which is utilized by means of circulation. In this case, it is sufficient to supply only acetyl phosphate as the phosphoric acid donator.

In the present invention, the enzymic reactions for synthesizing physiologically active substances by using ATP as an energy (hereinafter referred to as reaction system for physiologically active substance) may use one or more of the above-described synthetic reactions as the main reactions. Examples of them include a reaction for synthesizing peptide and peptide derivatives from amino acids by means of aminoacyl t-RNA synthetase, a reaction for synthesizing acetyl CoA or acyl CoA from acetic acid or aliphatic acid and CoA by means of acetyl CoA synthetase or acyl CoA synthetase, a reaction for synthesizing L-pantothenic acid from pantoic acid and β-alanine by means of pantothenic acid synthetase, a reaction for synthesizing guanylic acid from xanthylic acid and ammonia or glutamine by means of guanylic acid synthetase, a reaction for synthesizing asparagine from aspartic acid and ammonia by means of CoA from carboxylic acid and CoA by means of butyryl CoA synthetase, a reaction for synthesizing O-D-alanyl-poly-(ribitol phosphate) from D-alanine and poly(ribitol phosphate) by means of D-alanyl-poly(ribitol phosphate) synthetase and a reaction for synthesizing NAD+ from deamido NAD+ and L-glutamine by means of NAD+ synthetase, etc.

In the present invention, ATP is consumed in the above-described reaction system for making a physiologically active substance resulting the formation of AMP. The resulting AMP is converted into ATP using a combination of an enzyme which converts into ADP and an enzyme which converts into ATP, as described above (hereinafter referred to as the reaction system for reproduction of ATP).

In order to synthesize physiologically active substance from AMP as a raw material in the above-described reaction system for physiologically active substance, a reactor is first prepared. The reactor may be a membrane type reactor or a column type reactor. The membrane type reactor is particularly effective to use when the physiologically active substance is a low molecular material. In this case, since the enzymes are high molecular materials, each enzyme can be used by staying the enzyme in the reactor. The resulting AMP is eluted from the reactor because it is a low molecular material. After it is separated from the physiologically active substance by a simple operation such as ion-exchange chromatography, etc., it is sent back to the reactor, by which it is possible to reproduce ATP. Further, if the so-called water-soluble high molecular ATP which is obtained by previously introducing a suitable spacer into ATP and bonding to a water-soluble high molecular substance is used, the above-described operation for separation is not required. Various materials having a molecular weight of 1,000 to 500,000 may be used as the water-soluble high molecular substances. For example, it is possible to use polysaccharides such as a soluble dextran, vinyl polymer derivatives such as polyacrylamide derivatives or polyacrylic acid derivatives, and polyether derivatives such as polyethylene glycol derivatives, etc.

The column type reactor can be used without regard to the kind of physiologically active substance. When a column reactor is used, each enzyme is packed in the column in a form of the so-called immobilized enzyme which is prepared by bonding to, including in or absorbing in a suitable carrier as described above. In this reactor, the resulting AMP flows out of the reactor whether it is a high polymer or not, but it can be sent back to the reactor after being separated from the physiologically active substance in the same manner as described above. Further, in case of water-soluble high molecular ATP, the operation for separation can be easily carried out, because it can be separated by membrane separation.

The above-described reactor has been explained on the assumption that the operation is carried out continuously, and other rectors may be designed on the basis of such an idea. If necessary, a batch type reactor may be used in order to carry out a batchwise operation.

In the present invention, the reaction system for physiologically active substance and the reaction system for reproduction of ATP may be operated by combining them using different reactors, respectively. Further, the reaction system for physiologically active substance and the reaction system for reproduction of ATP may be operated in the same reactor. However, in order to synthesize the physiologically active substance efficiently, it is desirable to supply AMP produced in the reaction system for physiologically active substance to the reaction system for reproduction of ATP together with ATP, in both cases. In such cases, it is preferred that the ratio of AMP to ATP is in the range shown by the above-described formula (a).

In order to operate the reaction system for producing a physiologically active substance and the reaction system for reproduction of ATP by combining them using different reactors, it is possible to use, for example, the following method. First, to a reactor of the reaction system for reproduction of ATP, 0.1 $\mu$M to 4M, preferably 1 $\mu$M to 2M and, more preferably 10 $\mu$M to 500 mM of AMP, 0.1 $\mu$M to 500 mM, preferably 1 $\mu$M to 400 mM and, more preferably 10 $\mu$M to 300 mM of acetyl phosphate and ATP in an amount of, preferably, 4% or more based on AMP as shown in the formula (a), though it varies according to the ratio in the reaction system for reproduction of ATP, are fed to an end of the reactor together with AMP to carry out conversion of AMP→ADP→ATP in the reactor. The reacting solution eluted from the reactor is analyzed by a suitable analyzing system, by which concentrations of AMP, ADP and ATP and conversion to ATP can be determined. In this case, the flow rate varies according to the size of the reactor, and, for example, a suitable flow rate can be selected from the linear velocity range of $1\times10^{-4}$ cm/hr to $1\times10^6$ m/hr. A part of the reacting solution (the concentration of ATP is desired to be 4% or more based on the concentration of AMP) is circulated to send back to the inlet of the reactor and feeding of the ATP solution fed in the initial stage is stopped. The larger part of the reacting solution is fed immediately to the reactor of the reaction system for the physiologically active substance while controlling the concentration thereof together with substrates for the reaction system for the physiologically active substance in case that substance excepting ATP in the reacting solution, for example, acetic acid, do not inhibit the reaction system for the physiologically active substance, or it may be fed to an end of the reactor of the reaction system for the physiologically active substance together with a solution obtained by dissolving the substrates for the reaction system for the physiologically active substance after inhibiting substances are removed by a suitable separation means such as ion-exchange resin, etc., in case that they inhibit. In this case, the flow rate varies according to the size of the reactor, and a suitable flow rate may be selected, for example, from the linear velocity range of $1\times10^{-4}$ cm/hr to $1\times10^6$ m/hr. Concentrations of the substrates vary according to the physiologically active substance. When the solubility of the substrate is lower than the concentration of ATP fed from the reaction system for reproduction of ATP, the solubility of the substrate is the upper limit of concentration. Further, when the solubility of the substrate is higher than the concentration of ATP fed, the concentration is similar to the concentration of ATP is the highest concentration of the substrate. Further, in the latter case, if the ATP fed is concentrated, the synthetic reaction can be carried out at a higher concentration. In this case, operation becomes discontinuous because of the operation for concentration. The reaction product (physiologically active substance) and AMP are separated from the eluted solution in the reactor by a suitable separation means such as ion-exchange resin, and AMP is sent back to an end of the reactor of the reaction system for reproduction of ATP, by which ATP is reproduced again.

When the reaction system for producing a physiologically active substance and the reaction system for reproduction of ATP are operated in the same reactor, the operation can be carried out in only when substrates in both enzymic systems do not inhibit the enzymic reaction systems of each other. Concentrations of substrates in both enzymic reaction systems are desired to be selected according to a relation between the concentration of ATP produced in the reaction system for reproduction of ATP and the solubility of the substrate in the reaction system for physiologically active substance. For example, when the solubility of the substrate in the reaction system for physiologically active substance is lower than the concentration of ATP, concentrations of AMP, ATP and acetyl phosphate may be selected such that the concentration of ATP produced in the reaction system for reproduction of ATP agrees with the concentration of the substrate. In contrast with this, when the solubility of the substrate in the reaction system for physiologically active substance is higher than the concentration of ATP, it is desired that the concentration of the substrate is allowed to agree with the concentration of ATP produced in the reaction system for reproduction of ATP. It is preferred that the amount of ATP fed to the reaction system for reproduction of ATP together with AMP is more than 2 times, preferably more than 4 times and, more preferably, more than 5 times of the above-described case of using different reactors respectively. The flow rate varies according to the size of the reactor as well as the type of reactor, and a suitable flow rate can be selected from the linear velocity range, for example, $1\times10^{-4}$ cm/hr to $1\times10^6$ m/hr. Further, AMP and the physiologically active substance are separated from the reacting solution eluted from the reactor by means of a suitable separation means such as ion-exchange resin, etc., as described above, and AMP can be used again by sending back as a substrate to the inlet of the reactor.

In the present invention, the pH during the reaction varies according to enzyme used in case of the reaction system for physiologically active substance, but a pH in a nearly neutral range, namely, 6 to 11 and, preferably, 6.5 to 9.0 is generally used. In case of the reaction system for reproduction of ATP, a pH in the range of 6.5 to 11, preferably 6.5 to 9.0 and, more preferably 7 to 8 is used. As a buffer solution, it is possible to use conventional solutions fit for these pH ranges. For example, phosphates, imidazole salts, trishydrochloride, collidine salts and barbital hydrochloride, etc., can be used near pH 7. Further, the temperature for treatment can be selected from the range of room temperature to 50° C. In case of the reaction system for reproduction of ATP, though the reaction for reproduction of ATP may be carried out at a higher temperature, it is preferred to set at 5° C. or less which is the maximum growth temperature of enzyme producing microorganisms. Moreover, in order for the reaction of adenylate kinase and acetate kinase to effectively proceed in the reaction system for reproduction of ATP, various divalent metal ions can be used. As the divalent metal ions, magnesium ion and manganese ion are particularly recommended.

According to the present invention, change in conversion shown in the prior conversion of AMP into ATP can be overcome, and AMP can be converted effectively, continuously and economically into ATP at a conversion of substantial 100% over a long period of time. In addition, ATP conversion can be kept stably for a long period of time because of having good operation properties. Further, it is an advantage of the present invention that ATP converted from AMP in the packed bed type reactor can be used as a phosphoric acid donator. Moreover, as a starting material, pure AMP is not required, and mixtures of AMP with ADP and ATP may be used if they are controlled so as to satisfy the formula (a). Accordingly, the process is very advantageous for industrial use. Furthermore, the reaction system for reproduction of ATP can be advantageously applied to reproduction and utilization of ATP, and from a different point of view, it can be thought of as a process for production of ATP using AMP as a raw material.

ATP is an important material as a medicine and has been produced industrially. However, the fermentation process in the prior art has problems that byproducts are easily formed and productivity is inferior. Consequently, the price of ATP has been high. However, according to the present invention, such problems can be eliminated and ATP having high purity can be supplied with good productivity.

According to the present invention, the enzymic reaction using ATP as an auxiliary factor can be carried out continuously, effectively and economically by using the above-described reactors. Accordingly, it becomes possible to realize the operation of the so-called bioreactor wherein coupling reactions carried out in the living body are carried out as industrial chemical reactions outside the living body. Particularly, it is of great industrial value that protein synthesis reactions and peptide synthesis reactions by means of amino acid activating enzymes which are the most important reactions in the living body can be utilized for practical application.

In the following, the present invention is illustrated in greater detail in examples.

EXAMPLES 1-7

After 5 g of activated CH-Sepharose 4B (produced by Pharmacia Fine Chemicals) was washed to swell, 2,000 units of acetate kinase obtained from Bacillus stearothermophilus NCA 1503 (optimum growth temperature: 60° C.) (sold by Seikagaku Kogyo Co.) were added thereto and the reaction was carried out to obtain 1,000 units of immobilized acetate kinase. The same operation as described above was carried out using 250 units of adenylate kinase (sold by Seikagaku Kogyo Co.) instead of acetate kinase to obtain 100 units of immobilized adenylate kinase. The ratio of immobilized enzyme activity of acetate kinase to that of adenylate kinase in this case was 10.

A glass column having an inside diameter of 1.6 cm and a length of 10 cm was packed with both of these immobilized enzymes, and each substrate dissolved in a 25 mM imidazole hydrochloride buffer solution containing 10 mM magnesium chloride having a pH of 7.5 was fed to the column at a flow rate of 150 ml/hour. A variable fluid sending apparatus, an electromagnetic valve and a microcomputer were equipped on this column. The temperature in the column was kept at 30° C. Concentrations of AMP, ADP and ATP in the reacting solution eluted from the column were measured by a high performance liquid chromatographic apparatus. The concentration of AMP was fixed at 1.5 mM and the concentration of acetyl phosphate was fixed at 5 mM.

Conversion to ATP was then determined with varying the condition so as to satisfy the formula (a) by the microcomputer such that it was 0.063 mM ATP (ratio by concentration of ATP to AMP was 0.042; Example 1), 0.07 mM ATP (ratio by concentration of ATP to AMP was 0.047; Example 2), 0.13 mM ATP (ratio by concentration of ATP to AMP was 0.087; Example 3) and 0.19 mM ATP (ratio by concentration of ATP to AMP was 0.127; Example 4).

As a result, after feeding to the column, no AMP was detected after only 20 minutes and 98.5% of ATP and 1.5% of ADP were detected.

Further, the same procedure was carried out with varying the concentration of ATP to 0.03 mM ATP (ratio of concentration of ATP to AMP was 0.02; Example 5), 0.024 mM ATP (ratio by concentration of ATP to AMP was 0.016; Example 6) and 0.014 mM ATP (ratio of concentration of ATP to AMP was 0.009; Example 7).

As a result, 95% of ATP, 3% of ADP and 2% of AMP were detected in Example 5, 89% of ATP, 8% of ADP and 3% of AMP were detected in Example 6, and 72% of ATP, 20% of ADP and 8% of AMP were detected in Example 7.

EXAMPLE 8

After the reaction was initiated under the same condition as in Example 2, a solution eluted from the column after 20 minutes was circulated to feed to the column so that the ratio of ATP fed to the column to AMP was 0.047.

As a result, ATP was kept in the range of 98% to 98.5% over 5 hours after 20 minutes after the eluent from the reactor was used instead of ATP.

EXAMPLE 9

A glass column having an outside diameter of 2.0 cm and a length of 12 cm was packed with 2,000 units of immobilized acetate kinase and 200 units of immobilized adenylate kinase obtained by the same method as in Example 1, and 3.0 mM of AMP, 0.13 mM of ATP (ratio by concentration of ATP to AMP was 0.043) and 10 mM of acetyl phosphate which were dissolved in a 50 mM imidazole-hydrochloride buffer solution containing 25 mM magnesium chloride and 0.04% sodium azide having a pH of 7.5 were fed to the column at a flow rate of 300 ml/hour, and flow rates and concentrations of AMP and ATP were maintained so as to satisfy the formula (a).

As a result, the conversion to ATP was kept in the range of 98.5% to 99.0% over 10 days after initiation of the reaction.

EXAMPLE 10

After the reaction was initiated under the same condition as in Example 10, a solution eluted from the column after 30 minutes (containing 98% of ATP) was circulated to feed to the column so that the ratio by concentration of ATP fed to the column to AMP was 0.043.

As a result, the conversion to ATP was kept in the range of 98.2 to 98.7% over 10 days after initiation of the reaction.

EXAMPLE 11

Adenylate kinase and acetate kinase materials derived from available Bacillus stearothermophilus (sold by Seikagaku Kogyo Co.) were obtained. Acetyl CoA synthetase, a material derived from available yeast (produced by Boehringer Mannheim Co.) was also obtained.

These three enzymes were immobilized on Sepharose 4B as follows. Namely, after 5 g of activated CH-Sepharose 4B (produced by Pharmacia Fine Chemicals) was washed to swell, 2,000 units of acetate kinase were added thereto and the reaction was carried out to obtain 1,000 units of immobilized acetate kinase. Likewise, 100 units of immobilized adenylase were obtained from 250 units of adenylate kinase, and 10 units of immobilized acetyl CoA synthetase were obtained from 100 units of acetyl CoA synthetase. A column for reproduction of ATP (inside diameter: 1.6 cm, length: 10 cm) was packed with the immobilized acetate kinase and the immobilized adenylate kinase. 6 mM of AMP, 0.3 mM of ATP and 25 mM of acetyl phosphate which were dissolved in a 25 mM imidazole hydrochloride buffer solution containing 10 mM magnesium chloride having a pH of 7.5 were fed to the column at a flow rate of 25 ml/hour. The reaction temperature in the column was kept at 30° C. The resulting ATP was sent back to the inlet of the column in an amount of 5% (0.3 mM) based on the concentration of AMP.

Further, another column (inside diameter: 1.0 cm, length: 9 cm) was packed with immobilized acetyl CoA synthetase. As a substrate, 4 mM of potassium acetate, 4 mM of reduction type CoA, lithium salt and 4 mM of MgCl$_2$ which were dissolved in a 100 mM imidazole hydrochloride buffer solution having a pH of 7.5 were flown at a flow rate of 25 ml/hour, which was mixed with an ATP solution eluted from the reaction system for production of ATP in a ratio of 1:1. The mixture was fed to a column packed with the immobilized acetyl CoA synthetase (flow rate: 50 ml/hour, reaction temperature: 37° C.). Further, AMP was taken out from an elute from the column by means of Dowex 1-X8 (produced by the Dow Chemical Co.). After the pH and the concentrations were controlled to desired values, it was fed to the column for reproduction of ATP by means of a pump. The amount of the resulting acetyl CoA was measured by a method which comprises sampling 0.05 ml of the elute from the column, adding 3 ml of 1 mM 5,5'-dithiobis(2-nitrobenzoic acid) (DTNB) (pH 6.65, phosphoric acid buffer solution), determining the amount of unreacting SH group by change in absorbance in 412 nm at room temperature after the passage of 20 minutes, and calculating therefrom.

As a result, 1.5 mM of acetyl CoA was formed after 30 minutes from the initiation of the reaction, and thereafter a stabilized state was maintained over 24 hours.

EXAMPLE 12

A column (inside diameter: 1.8 cm, length: 12 cm) was packed with 2,000 units of immobilized acetate kinase, 200 units of immobilized adenylate kinase and 10 units of immobilized acetyl CoA synthetase which were obtained by the same methods as in Example 11, and 4 mM of AMP, 1.0 mM of ATP (25% based on the concentration of AMP), 25 mM of acetyl phosphate, 2.5 mM of potassium acetate and 2.5 mM of reduction type CoA lithium salt which were dissolved in a 100 mM imidazole hydrochloride buffer solution containing 10 mM magnesium chloride were fed thereto at a flow rate of 50 ml/hour. The reaction temperature in the column was kept at 37° C. AMP was separated from the solution eluted from the column by the same method as in Example 1 and it was sent back to the inlet for substrates. After 40 minutes from the initiation of the reaction, the formed acetyl CoA became 1.6 mM, and thereafter a stabilized state was kept over 15 hours.

EXAMPLE 13

To the same column for reproduction of ATP as in Example 11, 6 mM of AMP, 0.05 mM of ATP and 25 mM of acetyl phosphate which were dissolved in a 25 mM imidazole hydrochloride buffer solution containing 10 mM of magnesium chloride having a pH of 7.5 were fed at a flow rate of 25 ml/hour. A part of the solution eluted from the column was sent back to the inlet of the column for reproduction of ATP by the same method as in Example 11 in an amount of 0.05 mM as a concentration of ATP. Then, synthesis of acetyl CoA was carried out by the same column packed with immobilized acetyl CoA synthetase as in Example 11.

As a result, 1.0 mM of acetyl CoA was formed after 30 minutes from the initiation of the reaction, and thereafter a stabilized state was maintained over 24 hours.

EXAMPLE 14

Asparagine synthetase was produced from Lactobacillus arabinosus ATCC 8014 by carrying out ammonium sulfate fractionation, calcium phosphate gel treatment and gel filtration.

Using the same reaction system for reproduction of ATP as in Example 1, 4 mM of AMP, 0.3 mM of ATP (7.5% based on the concentration of AMP) and 16 mM of acetyl phosphate which were dissolved in a 25 mM imidazole hydrochloride buffer solution containing 10 mM manganese chloride having a pH of 7.5 were fed, and ATP was reproduced.

Further, 100 units of asparagine synthetase were dissolved in a 100 mM tris-hydrochloride buffer solution containing 4 mM of manganese chloride, and the resulting solution was enclosed in a membrane type reactor having an inside volume of 50 ml using an ultrafiltration membrane having a molecular weight of 30,000.

A 100 mM tris-hydrochloride buffer solution containing 4 mM manganese chloride in which 4 mM of ammonium chloride and 4 mM of L-asparatic acid were dissolved was mixed with an ATP solution obtained from the reaction system for reproduction of ATP in a ratio of 1:1 (by volume), and the resulting mixture was fed to the above-described reactor at a flow rate of 25 ml/hour. The reaction temperature in this case was kept at 37° C. AMP wa separated from the elute by the same method as in Example 1, which was sent back to the reaction system for reproduction of ATP. The amount of the formed L-asparagine was determined by applying the elute to a high performance liquid chromatographic apparatus.

As conditions for the chromatographic apparatus in this case, Shimadzu Zorbax ODS was used as the column and a mixture of 0.01M sodium acetate (pH 4.5)/acetonitrile (55/45 by volume) was used as an elute at a flow rate of 1 ml/min, and detection was carried out by measuring an absorbance in 210 nm.

As a result, 1.5 mM of L-asparagine was formed after 30 minutes from the initiation of the reaction, and thereafter a stabilized state was maintained over 15 hours.

EXAMPLE 15

Tyrosyl t-RNA synthetase was produced from Bacillus stearothermophilus: Deposition No. 5141 in Fermentation Research Institute by purifying through chromatography of DEAE-cellulose (produced by Whatman Ltd.), hydroxyapatite (sold by Seikagaku Kogyo Co.) and DEAE-Sephadex (produced by Pharmacia Fine Chemicals), ammonium sulfate fractionation and chromatgraphy of hydroxyapatite, DEAE-Sephadex and Sephadex G-150 (produced by Pharmacia Fine Chemicals).

Then, ATP (purity: 98%) was reproduced from AMP, a catalytic amount (5% based on the concentration of AMP) of ATP and acetyl phosphate by the same method as in Example 1, and it was used for the following reaction.

150 mg of the above-described purified tyrosyl t-RNA synthetase, 200 mg of magnesium chloride, 51 mg of ATP (purity: 98%), 0.5 mg of L-tyrosine, 100 units of pyrophosphatase (produced by Boehringer Mannheim) and 0.005 mg of dithiothreitol were dissolved in 70 ml of a 20 mM HEPES buffer solution (pH: 8.0), and they were allowed to react at 4° C. for 15 minutes to obtain a reaction mixture. To the resulting reaction mixture 2 g of L-phenylalanine methyl ester was added and well blended. The mixture was allowed to stand for 1 day with maintaining the reaction temperature at 30° C. to carry out the reaction.

To the resulting reacting solution, 100 ml of acetone was added. After precipitates were removed by centrifugal separation, the supernatant was concentrated to about 10 ml by an evaporator and processed by a high performance liquid chromatographic apparatus to separate a reaction product. As conditions for the chromatographic apparatus in this case, μBondapak $C_{18}$ (produced by Waters Associates) was used as the column and development was carried out using a solvent mixture of 50 mM phosphoric acid buffer solution (pH 7.0)/acetonitrile (85/15) and detection was carried out by measuring an absorbance in 210 nm.

As a result, 0.22 mg of L-tyrosyl-L-phenylalanine methyl ester was obtained. Further, AMP eluted in the void section was separated at the same time by the same method as in Example 11 and sent back to the reaction system for reproduction of ATP to reproduce ATP.

EXAMPLE 16

Methionyl t-RNA synthetase was obtained as a crude enzyme solution (purity: 10%) from available baker's yeast (produced by Oriental Yeast Co.) by operating with cellulose phosphate column chromatography.

Then, ATP (purity: 98%) was reproduced from AMP, a catalytic amount (5% based on the concentration of AMP) of ATP and acetyl phosphate by the same method as in Example 1, and it was used for the following reaction.

1 g of the above-described crude methionyl-t-RNA synthetase, 10 mg of magnesium chloride, 21 mg of ATP (purity: 98%), 0.5 mg of L-methionine, 5 units of pyrophosphatase (produced by Boehringer Mannheim) and 20 ml of mercaptoethanol were added to 15 ml of a 50 mM 2,5-dimethylimidazole buffer solution having a pH of 9.0. After being allowed to react by the same method as in Example 15, the reaction mixture was treated with Sephadex G-75 and elution was carried out with a HEPES buffer solution (pH: 8.0). 30 ml of a fraction in the void section was collected and the reaction mixture was isolated. To the isolated mixture, 0.5 g of L-leucine ethyl ester was added in a solid state and the reaction was carried out at 25° C. for 4 hours. To the resulting reaction product, 30 ml of acetone was added. After the formed precipitates were removed by centrifugal separation, the supernatant was concentrated to about 10 ml by an evaporator and separation was carried out by the same method as in Example 15 to obtain 0.92 mg of L-methionyl-L-leucin ethyl ester.

Further, ATP was reproduced from AMP by the same method as in Example 15.

While the invention has been described in detail and with reference to specific embodiments thereof, it will be apparent to one skilled in the art that various changes and modifications can be made therein without departing from the spirit and scope thereof.

What is claimed is:

1. A process for converting AMP into ATP comprising the steps of:
    providing separately or together a first enzyme and a second enzyme into a reactor, the first enzyme being capable of converting AMP into ADP and having been produced from microorganisms having an optimum growth temperature of 50° C. to 85° C., and the second enzyme being capable of converting ADP to ATP and having been produced from microorganisms having an optimum growth temperature of 50° C. to 85° C.;
    adding AMP into the reactor to form ATP;
    removing ATP from the reactor in an amount such that the reaction will continue to proceed to completion in the conversion of AMP into ATP, and
    mixing ATP as a phosphoric acid donor with AMP and adding the resulting mixture to the reactor,
    wherein the reaction is carried out at a temperature which retains desired activity; and
    wherein the mixing of AMP with ATP is carried out by controlling the concentration of ATP so as to satisfy the following formula (a):

$$0.15 \times \frac{5 + r^2}{r^2} \times AMP \geq ATP \geq 0.04 \times \frac{5 + r^2}{r^2} \times AMP \quad (a)$$

wherein AMP represents the concentration of AMP (mM), ATP represents the concentration of ATP (mM), and r represents a ratio of immobilized enzyme activity of the enzyme which converts ADP into ATP to immobilize enzyme activity of the enzyme which converts AMP into ADP, which is a positive integer of 1 or more.

2. A process for converting AMP into ATP as claimed in claim 1, wherein the first enzyme which converts AMP into ADP is adenylate kinase and the second enzyme which converts ADP into ATP is acetate kinase.

* * * * *